United States Patent
Han et al.

(10) Patent No.: US 10,287,554 B2
(45) Date of Patent: May 14, 2019

(54) INDUCED PLURIPOTENT STEM CELL MODEL FOR FABRY DISEASE AND USE THEREOF

(71) Applicant: KOREA ADVANCED INSTITUTE OF SCIENCE AND TECHNOLOGY, Daejeon (KR)

(72) Inventors: Yong-mahn Han, Daejeon (KR); Sang-Wook Park, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 506 days.

(21) Appl. No.: 14/839,603

(22) Filed: Aug. 28, 2015

(65) Prior Publication Data
US 2015/0361401 A1     Dec. 17, 2015

Related U.S. Application Data

(63) Continuation of application No. PCT/KR2013/012020, filed on Dec. 23, 2013.

(30) Foreign Application Priority Data

Dec. 23, 2013  (KR) .................. 10-2013-0160920

(51) Int. Cl.
*C12N 5/074*  (2010.01)
*G01N 33/50*  (2006.01)

(52) U.S. Cl.
CPC ...... *C12N 5/0696* (2013.01); *G01N 33/5064* (2013.01); *C12N 2501/602* (2013.01); *C12N 2501/603* (2013.01); *C12N 2501/604* (2013.01); *C12N 2501/606* (2013.01); *C12N 2506/1307* (2013.01)

(58) Field of Classification Search
None
See application file for complete search history.

(56) References Cited

U.S. PATENT DOCUMENTS
2015/0362483 A1* 12/2015 Blackman

FOREIGN PATENT DOCUMENTS
KR  10-2013-0133598   12/2013
WO  WO 2015/099206 A1  7/2015

OTHER PUBLICATIONS

Maury, Y. et al., "Human pluripotent stem cells for disease modelling and drug screening", Bioessays, 2011, vol. 34: pp. 61-71.*
Itzhaki et al, "Modelling the long QT syndrome with induced pluripotent stem cells", Nature, 2011, vol. 471: pp. 225-230.*
Kawagoe, et al., "Morphological features of iPS cells generated from Fabry disease skin fibroblasts using Sendai virus vector (SeVdp)," *Molecular Gentics and Metabolism*, 109:386-389 (2013).
Meng et al., "A mechanistic study of Fabry heart disease using induced pluripotent stem cells," *The American Society of Human Genetics 61th Annual Meeting*, Program No. 1319T (Published Oct. 13, 2011) (Abstract only).
Meng et al., "Induced pluripotent stem cells derived from mouse models of lysosomal storage disorders," *PNAS*, 107(17):7886-7891 (2010).
Rufaihah, et al., "Human induced pluripotent stem cell-derived endothelial cells exhibit functional heterogeneity," *Am J Transl Res.*, 5(1):21-35 (2013).
International Search Report issued in International Application No. PCT/KR2013/012020 dated Aug. 28, 2014 (6 pages) (in Korean with English translation).

* cited by examiner

*Primary Examiner* — Michael D Burkhart
(74) *Attorney, Agent, or Firm* — Klarquist Sparkman, LLP

(57) ABSTRACT

The present invention relates to an induced pluripotent stem cell model of Fabry disease, a preparation method thereof, and a use of the same for the study of Fabry disease development and for the screening of a therapeutic agent for the disease. Particularly, Fabry disease derived induced pluripotent stem cells (iPSCs), embryoid body (EB), and vascular cells were developed and differentiated from fibroblasts originated from Fabry disease patient, wherein the Fabry disease originated iPSCs displayed significantly reduced expression and activity of GLA protein therein, compared with the normal cells, resulting in the accumulation of globotriaosylceramide (Gb3, CD77). Also, the differentiation of vascular cells was induced from the Fabry disease originated iPSCs, and as a result the iPSCs were successfully differentiated into vascular endothelial cells and vascular smooth muscle cells with significantly expressing the marker protein. When the vascular endothelial cells and vascular smooth muscle cells were treated with Fabrazyme, the accumulation of Gb3 was significantly reduced, suggesting that the said cell model can be effectively used for the analysis/study of Fabry disease outbreak mechanism and for the screening of a therapeutic agent for the disease.

12 Claims, 15 Drawing Sheets
Specification includes a Sequence Listing.

[Fig. 1]
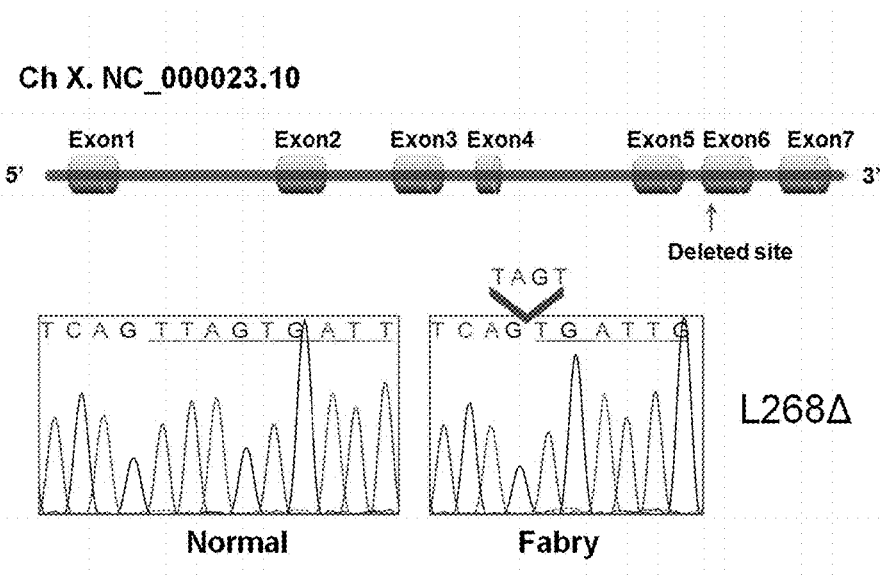

[Fig. 2]
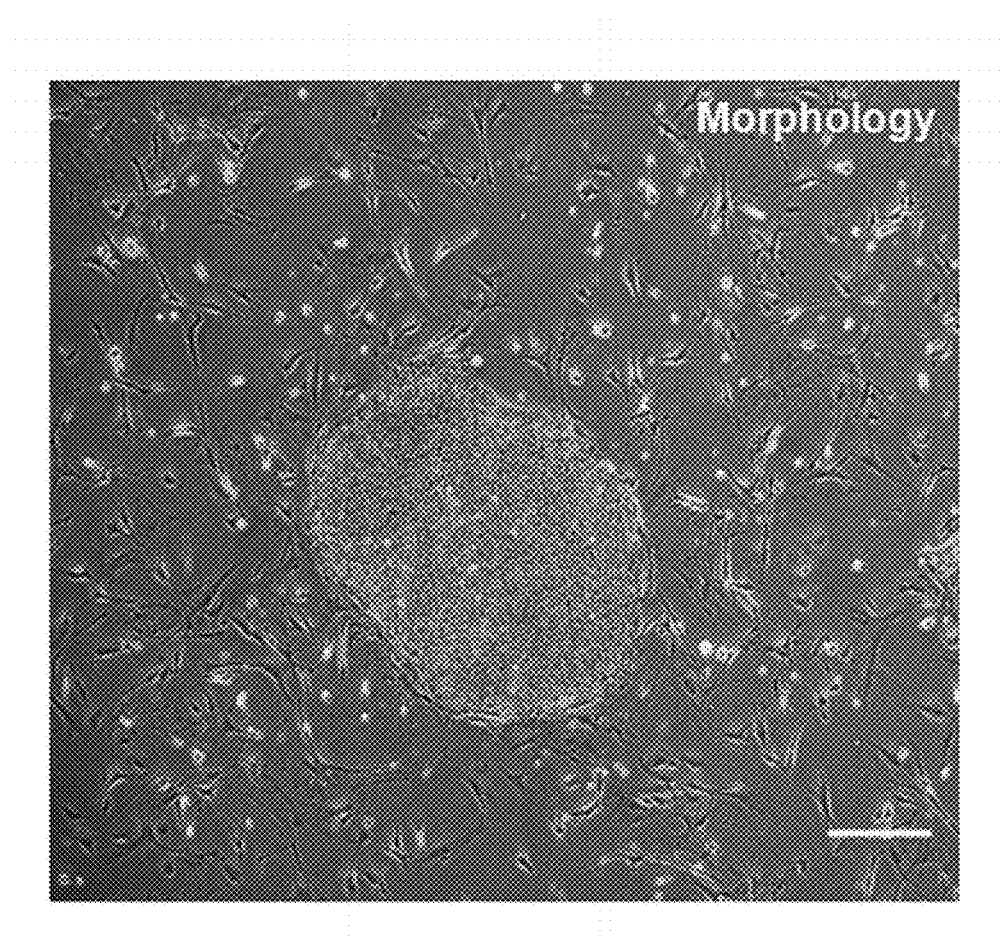

[Fig. 3]
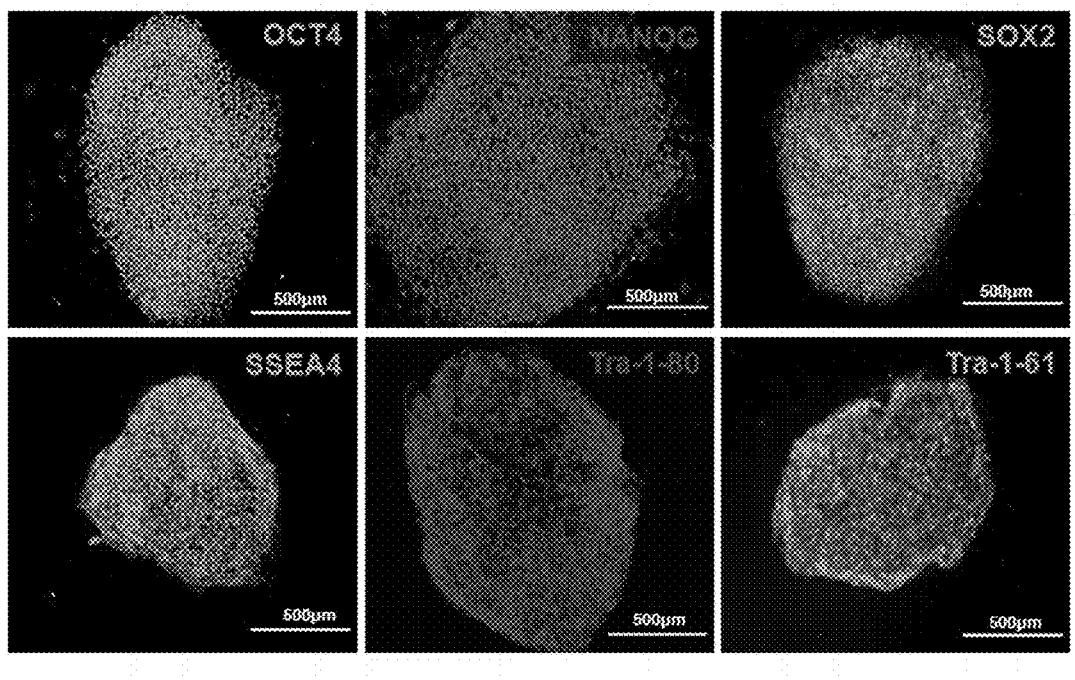

[Fig. 4]
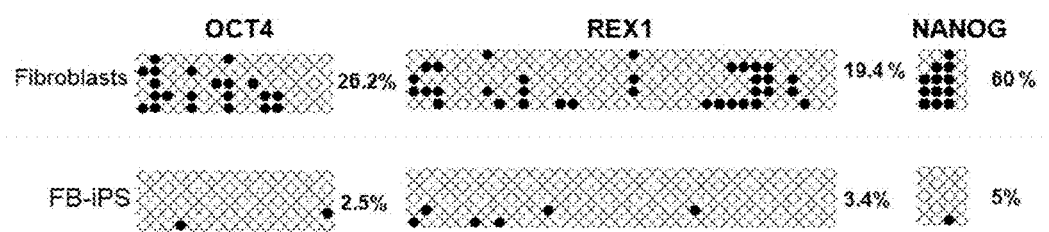

[Fig. 5]
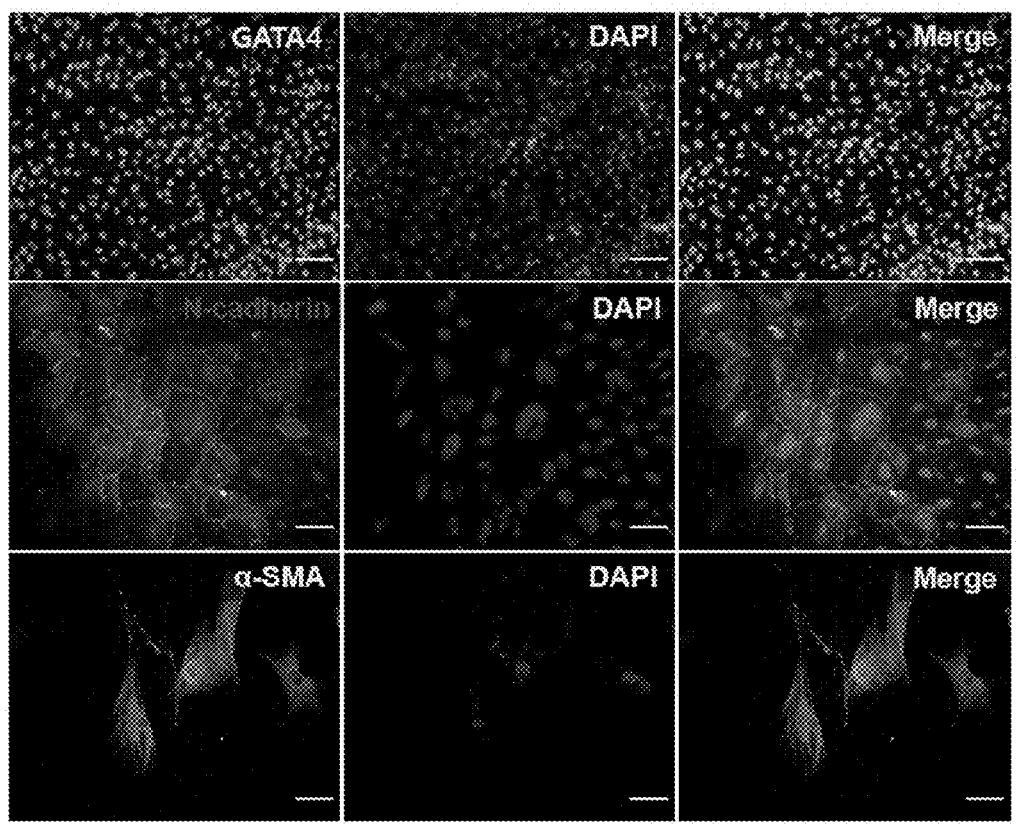

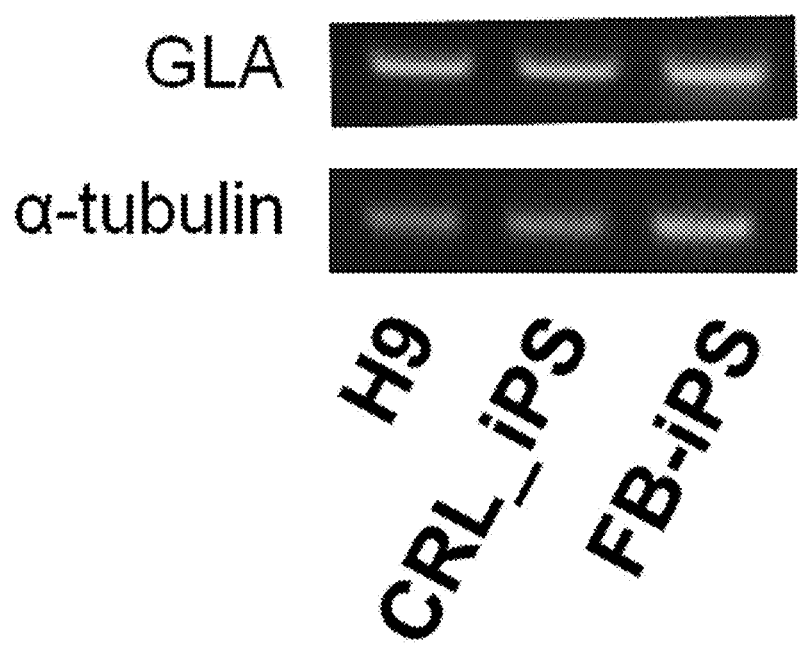
[Fig. 6]

[Fig. 7]
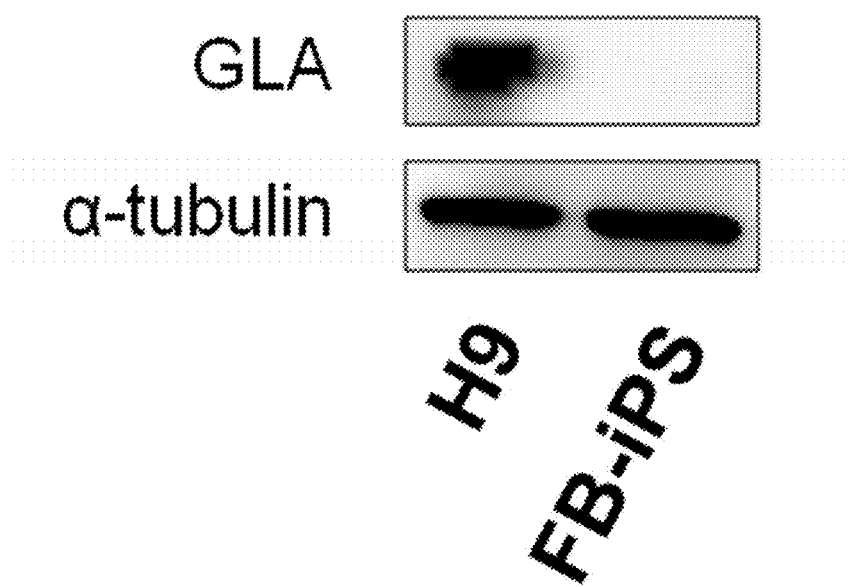

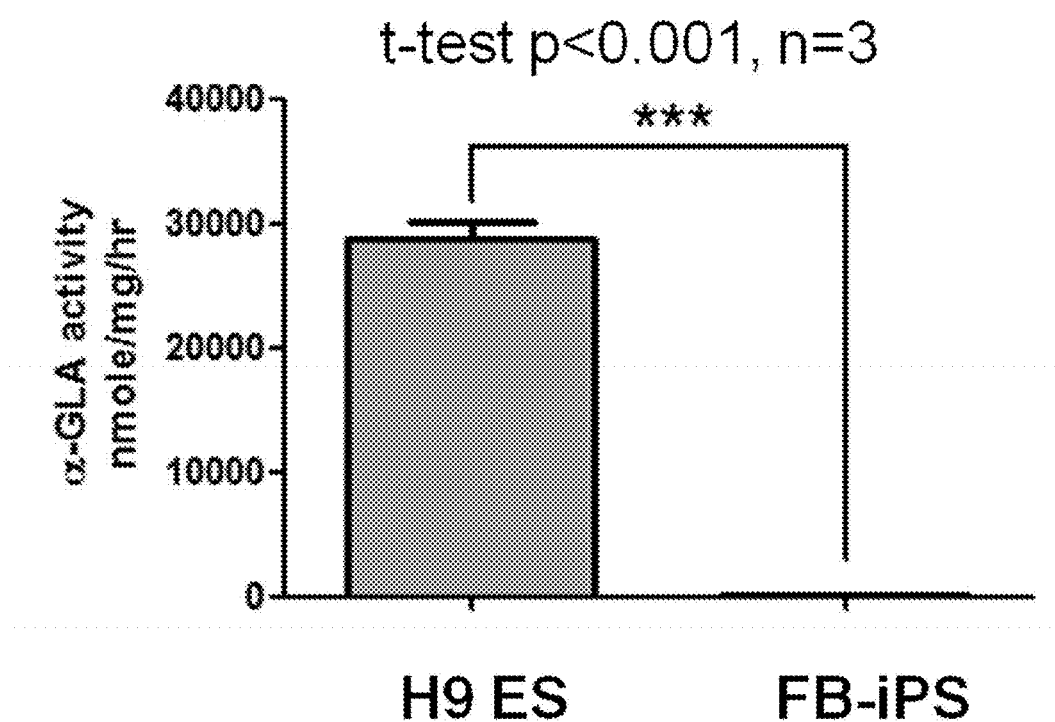
[Fig. 8]

[Fig. 9]
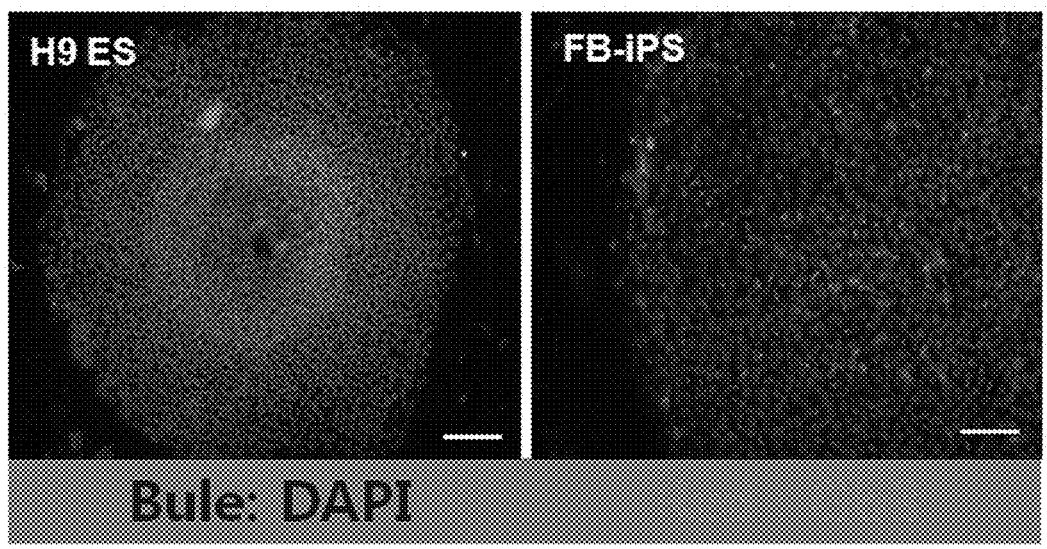

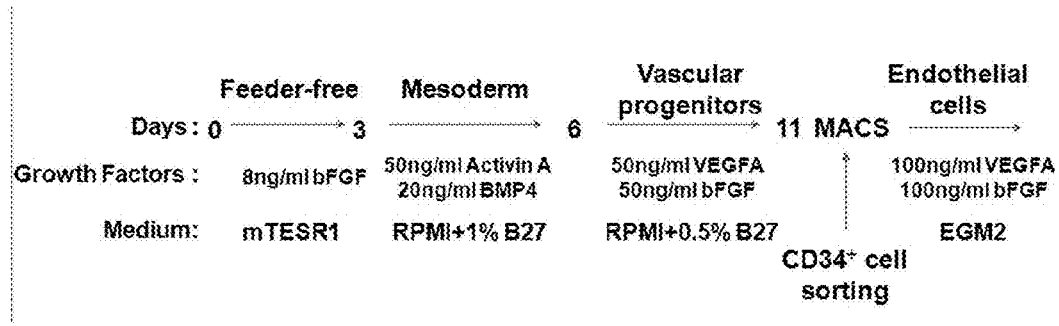
[Fig. 10]

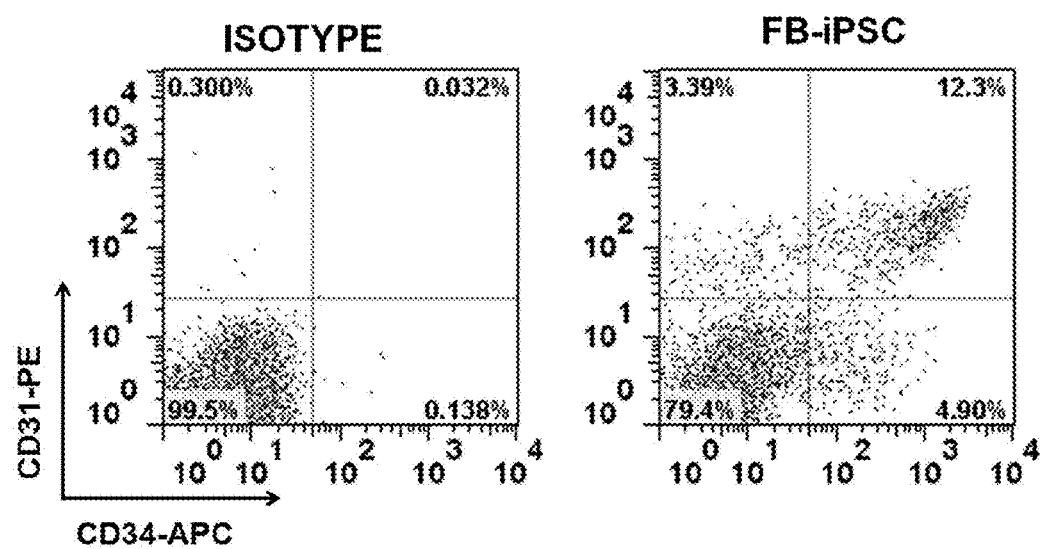
[Fig. 11]

[Fig. 12]
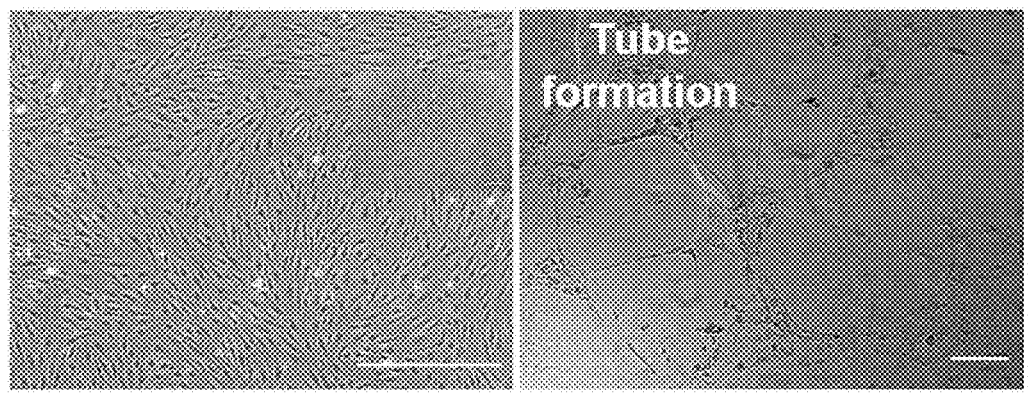

[Fig. 13]
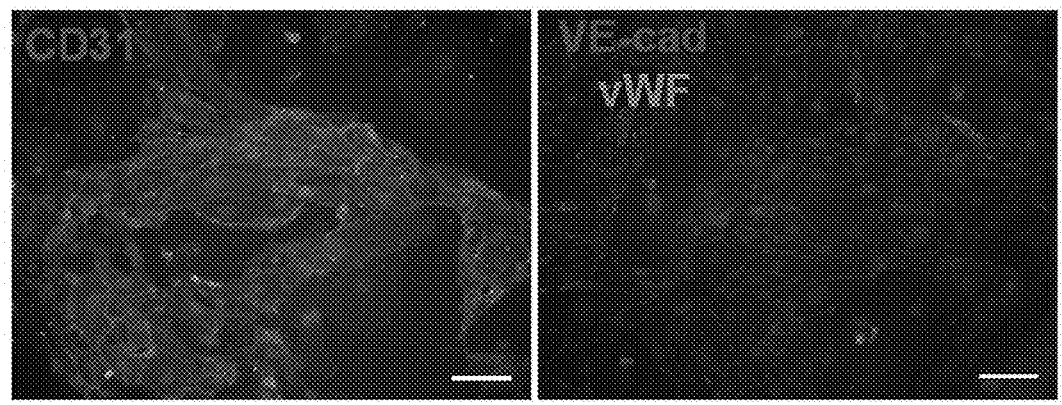

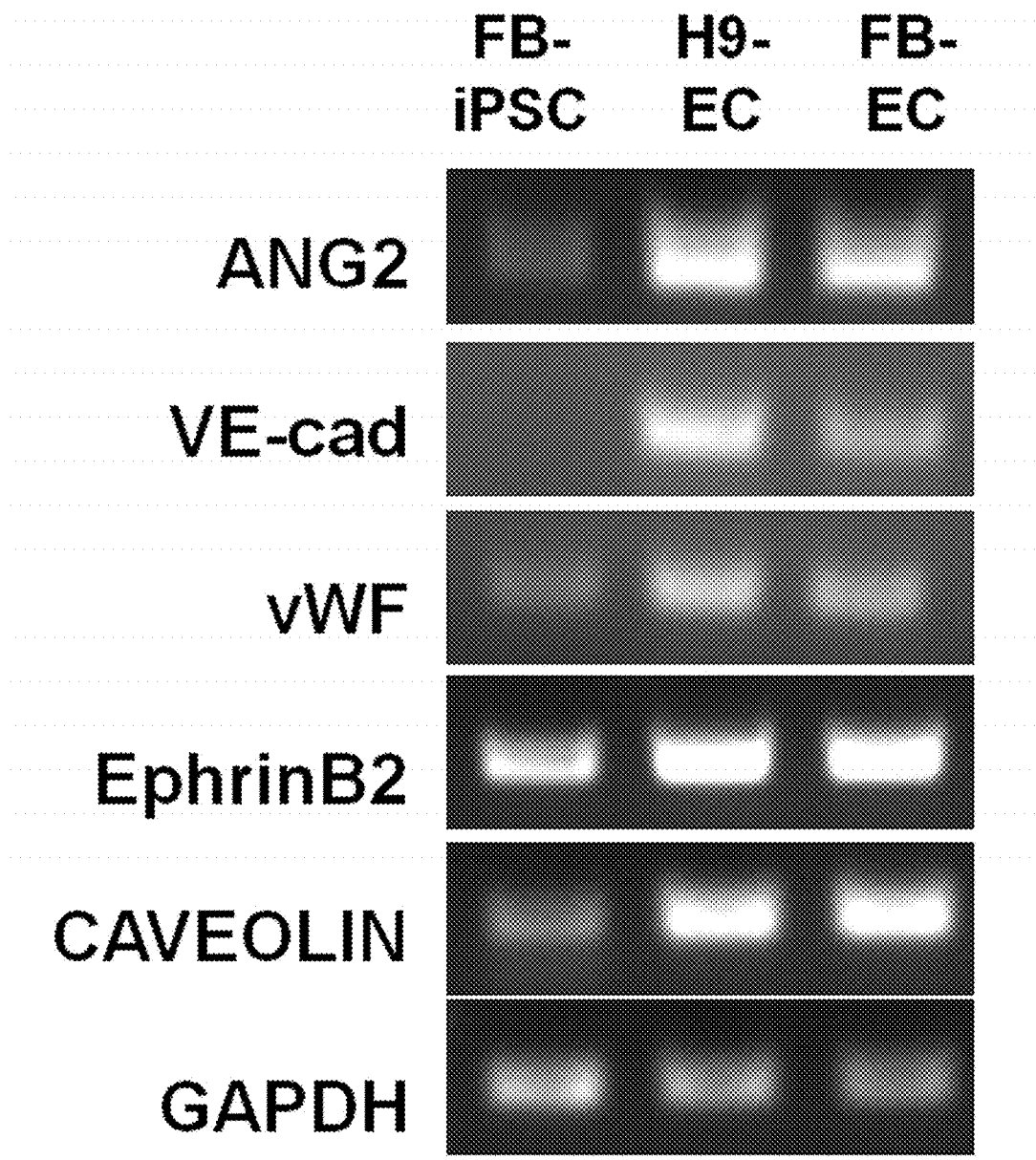
[Fig. 14]

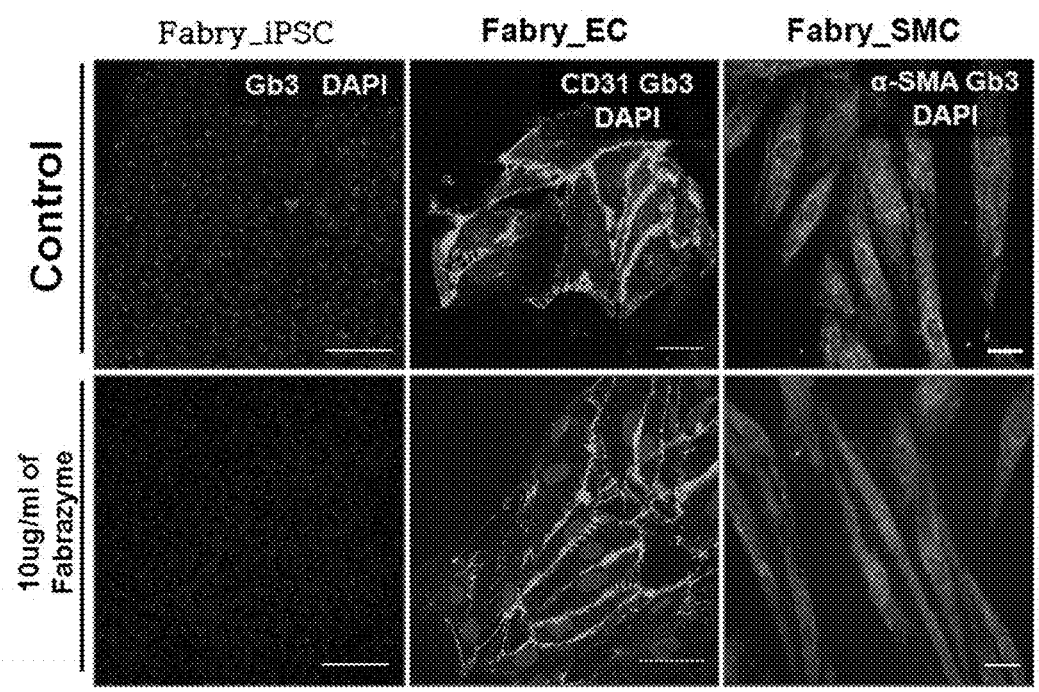
[Fig. 15]

INDUCED PLURIPOTENT STEM CELL MODEL FOR FABRY DISEASE AND USE THEREOF

CROSS REFERENCE TO RELATED APPLICATIONS

This is a continuation of PCT Application No. PCT/KR2013/012020, filed on Dec. 23, 2013, which is incorporated by reference, and which claims priority to Korean Application No. 10-2013-0160920, filed on Dec. 23, 2013.

BACKGROUND OF THE INVENTION

1. Field of the Invention

The present invention relates to an induced pluripotent stem cell (iPSC) model of Fabry disease, a preparation method thereof, and a use of the same for the study of Fabry disease development and for the screening of a therapeutic agent for the disease.

2. Description of the Related Art

Fabry disease is a X-gene related recessive disorder caused by mutation of GLA that is the gene encoding α-galactosidase (GLA). The said GLA gene resides on xq22.1 of #7 exon, and encodes a glycoprotein that is composed of 370 amino acids which is processed from a precursor protein composed of 429 amino acids (Schiffmann, R. *Pharmacology & therapeutics* 122, 65-77 (2009)). According to the previous report, the incidence rate of Fabry disease is 1 out of 117,000 males (Meikle, P. J. et al. *Jama* 281, 249-254 (1999)). However, according to the most recent screening, the incidence rate is rapidly increasing and is diagnosed in 1 boy out of 3100~3700 boys (Spada, M. et al. *American journal of human genetics* 79, 31-40 (2006)).

Once the lysosomal enzyme is deficient because of GLA gene mutation, globotriaosylceramide (Gb3, CD77) which is the neutral glycosphingolipid known to be acting as a Shiga toxin receptor in Burkitt's lymphoma cells is excessively accumulated, which seems to be the reason of Fabry disease (Nudelman, E. et al. *Science New York, N.Y* 220, 509-511 (1983)).

Up to date, approximately at least 400 mutation sites have been known as the possible mutation site in GLA gene (http://www.hgmd.cf.ac.uk). Symptoms of Fabry disease vary from the mutation site of GLA gene. In most mutation cases, α-galactosidase activity disappears. Missense mutations take 5~10%, and clinically important major pathophysiology is not caused with the remaining enzyme activity (Clarke, J. T. *Annals of internal medicine* 146, 425-433 (2007)).

The major pathophysiological symptom shown in Fabry disease patients is Gb3 accumulation in various cells such as vascular cells, cardiac cells, kidney epithelial cells, and neuronal cells. In particular, Gb3 accumulation in vascular cells causes systemic cardiovascular dysfunction exemplified by stroke or myocardial infraction.

The only treatment method for Fabry disease is repetitive enzyme replacement therapy, wherein the α-galactosidase 'Fabrazyme' belonging to agalsidase beta (Eng, C. M. et al. *The New England journal of medicine* 345, 9-16 (2001)) or 'Replagal' belonging to agalsidase alpha (Schiffmann, R. et al. *Proceedings of the National Academy of Sciences of the United States of America* 97, 365-370 (2000)) is administered to Fabry disease patient to eliminate Gb3 accumulated in various cells. The intravenously injected enzyme is introduced in cells via mannose 6 phosphate (M6P) receptor in plasma membrane, and then further moves to lysosome. The administration of such therapeutic enzyme plays a key role in treating Fabry disease. However, those recombinant enzymes like Fabrazyme and Replagal are unstable in blood and might cause allergic reaction if they are repeatedly administered (Eng, C. M. et al. *The New England journal of medicine* 345, 9-16 (2001); Schiffmann, R. et al. *Proceedings of the National Academy of Sciences of the United States of America* 97, 365-370 (2000); Sakuraba, H. et al. *Journal of human genetics* 51, 180-188 (2006)).

To study Fabry disease and to develop a treating agent for the disease, it is the general manner to establish GLA knock-out mouse and to investigate the involvement of Gb3 accumulation in endothelial dysfunction. The abnormal accumulation of Gb3 was observed in caveolae of aortic endothelial cells in the GLA knock-out mouse (Shu, L. & Shayman, J. A. *The Journal of biological chemistry* 282, 20960-20967 (2007)). According to the previous report, such abnormal Gb3 deposit induced dysfunction of calcium channel in the GLA knock-out mouse endothelial cells (Park, S. et al. *Cardiovascular research* 89, 290-299 (2010)).

Even though vasculopathy was found in the GLA knock-out mouse as the Fabry disease model system caused by the lack of α-galactosidase A from various research attempts, the precise mechanism of cardiovascular complication induced by the deficiency of α-galactosidase A activity and the resulting Gb3 deposit in vascular cells has not been disclosed, yet. It is expected that the limit of study on the outbreak mechanism of Fabry disease can be overcome by using iPSCs originated from Fabry disease patient somatic cells.

Stem cells are the cells in the phase of pre-differentiation before being differentiated into each tissue forming cells, which can be obtained from the tissues of an embryo, a fetus, and an adult. Stem cells have self-proliferative activity that makes unlimited proliferation possible from undifferentiated status and have pluripotency, so that they can be differentiated into various tissue cells once a certain stimulus is given. That is, stem cells become differentiated by a certain differentiation stimulus (environment), and are self-renewal so as to produce those cells that are same as themselves by cell division, unlike the differentiated cells whose cell division has been finished. Stem cells also have plasticity, by which stem cells can be differentiated into different cells when the environment is changed or when a different stimulus is provided.

Human pluripotent stem cells including induced pluripotent stem cells (induced pluripotent stem cells; iPSCs) are characterized by pluripotency which is the ability to be differentiated into various types of cells. Therefore, when iPSCs are used for in vitro differentiation system, they can be efficiently used for the evaluation of not only therapeutic potential owing to the low risk of immune rejection but also complicated disease mechanism particularly in relation to the early development stage of organogenesis (Muotri, A. R. (2009) Epilepsy Behav 14 Suppl 1: 81-85; Marchetto, M. C., B. Winner, et al. (2010) Hum Mol Genet 19(R1): R71-76).

It has been reported that when the iPSCs originated from patients having different genetic diseases were induced to be differentiated into disease-related cells, the cells displayed disease-specific phenotype (Park, I. H. et al. *Cell* 134, 877-886 (2008); Tiscornia, G. et al. *Nature medicine* 17, 1570-1576 (2011)). That is, such disease-specific iPSCs can be differentiated into disease-related cells and therefore they can be effectively used for the study of specific mechanism of disease and for the screening of a therapeutic agent.

Thus, the present inventors tried to establish a stem cell model for the study of Fabry disease. In the course, the inventors induced the development and differentiation of Fabry disease originated induced pluripotent stem cells (iPSCs), embryoid body (EB), and vascular cells from the fibroblasts of Fabry disease patient and confirmed that Gb3 was accumulated in the iPSCs by the significantly reduced expression and activation of GLA protein. The inventors also induced the differentiation of vascular cells from Fabry disease originated iPSCs. As a result, the said iPSCs were differentiated into vascular endothelial cells and vascular smooth muscle cells wherein the marker protein was significantly expressed. When the vascular endothelial cells and vascular smooth muscle cells were treated with Fabrazyme, the accumulation of globotriaosylceramide (Gb3, CD77) was significantly reduced. Therefore, the present inventors confirmed that the Fabry disease cell modeling method using induced pluripotent stem cells (iPSCs) of the invention can be efficiently used for the study of Fabry disease development and for the screening of therapeutic agent candidates, leading to the completion of this invention.

SUMMARY OF THE INVENTION

It is an object of the present invention to provide a method for using the novel induced pluripotent stem cells (iPSCs) demonstrating the same characteristics as Fabry disease patient cells for the study of Fabry disease development and for the screening of therapeutic agent candidates for the disease.

To achieve the above objects, the present invention provides

To achieve the above object, the present invention provides a method for preparing a Fabry disease iPSC model in vitro comprising the following steps:

i) inducing the differentiation of induced pluripotent stem cells (iPSCs) from the fibroblasts separated from Fabry disease patient in vitro; and ii) collecting the iPSCs induced in step i).

The present invention also provides a Fabry disease iPSC model prepared by the method above.

The present invention further provides a method for using iPSCs as a Fabry disease model comprising the following steps:

i) inducing the differentiation of embryoid body (EB) or vascular cells from the iPSCs prepared above; and ii) analyzing the differentiation marker for the embryoid body or the vascular cells induced in step i).

The present invention also provides a method for the screening of therapeutic agent candidates for Fabry disease comprising the following steps:

i) treating the iPSC model or the embryoid body or vascular cells differentiated from the same with the sample compound or composition;

ii) analyzing the characteristics of the iPSC model, embryoid body, or vascular cells of step i); and iii) comparing the results of step ii) with the analysis result of the non-treated control.

The present invention also provides a use of the Fabry disease iPSC model prepared by the above method.

In addition, the present invention provides a use of iPSCs as a Fabry disease model comprising the following steps:

i) inducing the differentiation of embryoid body (EB) or vascular cells from the iPSCs prepared above; and ii) analyzing the differentiation marker for the embryoid body or the vascular cells induced in step i).

ADVANTAGEOUS EFFECT

The stem cell model of the present invention using the induced pluripotent stem cells (iPSCs) originated from the fibroblasts of Fabry disease patient has been confirmed to be useful for the investigation of differentiation of vascular cells and the intracellular globotriaosylceramide (Gb3, CD77) deposit which is the major symptom of Fabry disease, so that this model can be efficiently used for the study of Fabry disease outbreak mechanism and for the screening of therapeutic agent candidates.

BRIEF DESCRIPTION OF THE DRAWINGS

The application of the preferred embodiments of the present invention is best understood with reference to the accompanying drawings, wherein:

FIG. 1 presents the mutation of GLA that is the causing gene of Fabry disease in the induced pluripotent stem cells (iPSCs) originated from the fibroblasts of Fabry disease patient.

FIG. 2 presents the development of Fabry disease originated iPSC (FB-iPSC).

FIG. 3 presents the expression patterns of the stem cell markers OCT4, NANOG, SOX2, SSEA4, Tra-1-80, and Tra-1-61 proteins in order to confirm the pluripotency of FB-iPSC.

FIG. 4 illustrates bisulfite sequencing of non-differentiated FB-iPSC to investigate DNA methylation.

FIG. 5 illustrates the expression patterns of the ectodermal marker N-cadherin, the endodermal marker SOX17, and the mesodermal marker α-smooth muscle actin in the embryoid body (EB) differentiated from FB-iPSC.

FIG. 6 presents the expression level of α-galactosidase (GLA) gene in FB-iPSC.

FIG. 7 presents the expression level of GLA protein in FB-iPSC.

FIG. 8 presents the deficiency of GLA enzyme activity in FB-iPSC.

FIG. 9 illustrates the deposit of globotriaosylceramide (Gb3, CD77) in FB-iPSC.

FIG. 10 is a schematic diagram illustrating the differentiation of vascular endothelial cells and vascular smooth muscle cells induced from FB-iPSC.

FIG. 11 presents magnetic activated cell sorting (MACS) for the separation of those cells expressing CD31 and CD34 simultaneously among the vascular progenitors differentiated from FB-iPSC.

FIG. 12 presents the cell morphology of the vascular endothelial cells differentiated from FB-iPSC.

FIG. 13 illustrates the expression patterns of the vascular endothelial cell marker proteins CD31, VE-cadherin, and vWF in the vascular endothelial cells differentiated from FB-iPSC.

FIG. 14 illustrates the expression patterns of the vascular endothelial cell-specific marker genes ANG2, VE-cad, vWF, EphrinB2, and CAVEOLIN in the vascular endothelial cells differentiated from FB-iPSC.

FIG. 15 illustrates the Gb3 deposit inhibiting effect of α-galactosidase in FB-iPSC, FB-iPSC originated vascular endothelial cells, and FB-iPSC originated vascular smooth muscle cells.

SEQUENCE LISTING

The Sequence Listing is submitted as an ASCII text file in the form of the file named Sequence_Listing.txt, which was created on Aug. 28, 2015, and is 1,117 bytes, which is incorporated by reference herein.

DESCRIPTION OF THE PREFERRED EMBODIMENTS

Hereinafter, the present invention is described in detail.

The present invention provides a method for preparing a Fabry disease iPSC model in vitro comprising the following steps:

i) inducing the differentiation of induced pluripotent stem cells (iPSCs) from the fibroblasts separated from Fabry disease patient in vitro; and ii) collecting the iPSCs induced in step i).

In step i), the inducement is preferably achieved by the ectopic expression of the pluripotent marker such as OCT4, SOX2, KLF4, and C-MYC, but not always limited thereto.

In a preferred embodiment of the present invention, the present inventors prepared iPSC originated from Fabry disease patient (FB-iPSC) and confirmed the mutation of GLA therein (see FIGS. 1 and 2). The said FB-iPSC displayed the stemness marker expressed therein (see FIG. 3) and was confirmed to finish with reprogramming as in the non-differentiated status (see FIG. 4).

Therefore, the Fabry disease originated iPSC model of the present invention displays pluripotency with showing the same mutation as Fabry disease patients have, so that the method for preparing the said iPSC model can be effectively used for the study of Fabry disease.

The present invention also provides a Fabry disease iPSC model prepared by the method above.

The iPSC mentioned above is characterized by one or more characteristics selected from the group consisting of the below a)~e), but not always limited thereto;

a) expressing one or more pluripotency markers selected from the group consisting of OCT4, NANOG, SOX2, SSEA4, Tra-1-80, and Tra-1-61;

b) expressing α-galactosidase (GLA) gene;

c) incapable of expressing GLA protein;

d) lack of GLA enzyme activity; and e) intracellular globotriaosylceramide (Gb3, CD77) deposit.

The Fabry disease originated iPSC model of the present invention displays pluripotency with showing the same mutation as Fabry disease patients have, so that the said iPSC model can be effectively used for the study of Fabry disease.

The present invention further provides a method for using the iPSCs as a Fabry disease model comprising the following steps:

i) inducing the differentiation of embryoid body (EB) or vascular cells from the iPSCs prepared above; and ii) analyzing the differentiation marker for the embryoid body or the vascular cells induced in step i).

The embryoid body differentiation marker herein is preferably selected from the group consisting of the ectodermal marker N-cadherin, the endodermal marker SOX17, and the mesodermal marker α-smooth muscle actin, but not always limited thereto.

The vascular cells above are preferably vascular endothelial cells or vascular smooth muscle cells, but not always limited thereto.

The said vascular endothelial cells are characterized by one or more characteristics selected from the group consisting of the following a)~c), but not always limited thereto;

a) having vascular tube like structure;

b) expressing one or more vascular endothelial cell markers selected from the group consisting of CD31, VE-cadherin, and vWF; and c) expressing one or more vascular endothelial cell marker genes selected from the group consisting of ANG2, VE-cad, vWF, EphrinB2, and CAVEOLIN.

In another preferred embodiment of the present invention, the present inventors induced the differentiation of embryoid body (EB) from FB-iPSC (FB-EB). As a result, the expressions of three germ layer markers such as the ectodermal marker N-cadherin, the endodermal marker SOX17, and the mesodermal marker α-smooth muscle actin were confirmed in the differentiated FB-EB, suggesting that the FB-EB had pluripotency (see FIG. 5).

The present inventors also investigated GB3 deposit induced by the lack of GLA activity, which is the cause of Fabry disease, in FB-iPSCs. As a result, the expression of GLA gene in FB-iPSC was similar to the level in normal cells (see FIG. 6), while GLA protein was not expressed therein (see FIG. 7). Therefore, it was confirmed that FB-iPSCs were confirmed to be lack of GLA protein activity (see FIG. 8) and thus to display intracellular Gb3 deposit (see FIG. 9).

The present invention also induced the differentiation of vascular progenitors or vascular cells from FB-iPSC (see FIGS. 10 and 11). As a result, the vascular cells differentiated from FB-iPSC were differentiated into vascular endothelial cells and vascular smooth muscle cells (see FIG. 12). In the vascular endothelial cells, the expressions of the vascular endothelial cell marker proteins such as CD31, VE-cadherin (VE-cad), and vWF were confirmed (see FIG. 13) along with the expressions of the vascular endothelial cell-specific marker genes such as ANG2, VE-cad, vWF, EphrinB2, and CAVEOLIN (see FIG. 14).

The Fabry disease originated iPSC model of the present invention kept the same pluripotency as the normal iPSCs showed, and accordingly it can be efficiently differentiated into embryoid body or vascular cells. However, the expression and activity of GLA protein, which is characteristically shown in Fabry disease patient originated cells, were not as high as in the normal iPSCs, suggesting that Gb3 deposit would be induced. So, the iPSC model of the invention can be effectively used for the study of Fabry disease including the development of a method for the diagnosis of Fabry disease and a method for the screening thereof.

The present invention also provides a method for the screening of therapeutic agent candidates for Fabry disease comprising the following steps:

i) treating the iPSC model or the embryoid body or vascular cells differentiated from the same with the sample compound or composition;

ii) analyzing the characteristics of the iPSC model, embryoid body, or vascular cells of step i); and iii) comparing the results of step ii) with the analysis result of the non-treated control.

To analyze the characteristics of the iPSC model of step ii), the pluripotency of the iPSC model to be differentiated into embryoid body or vascular cells is preferably investigated, but not always limited thereto.

The characteristics of the embryoid body of step ii) preferably indicates the expression of one or more proteins selected from the group consisting of N-cadherin, SOX17, and α-smooth muscle actin, but not always limited thereto.

The characteristics of the vascular cells of step iii) are preferably one or more characteristics selected from the group consisting of the following a)~d), but not always limited thereto The said vascular endothelial cells are characterized by one or more characteristics selected from the group consisting of the below a)~d), but not always limited thereto;
 a) having vascular tube like structure;
 b) showing reduced Gb3 deposit;
 c) expressing one or more vascular endothelial cell markers selected from the group consisting of CD31, VE-cadherin, and vWF; and
 d) expressing one or more vascular endothelial cell marker genes selected from the group consisting of ANG2, VE-cad, vWF, EphrinB2, and CAVEOLIN.

The vascular cells above are preferably vascular endothelial cells or vascular smooth muscle cells, but not always limited thereto.

The comparison in step iv) is performed to select a sample compound or composition that preserves the pluripotency in the iPSCs as same as shown in the normal iPSCs when it is treated. Precisely, it is preferred to select a sample compound or composition that demonstrates either the recovery of GLA protein expression and activity or the decrease of Gb3 deposit or both of them, but not always limited thereto.

The comparison in step iv) is performed preferably to select a sample compound or composition that preserves the pluripotency in the embryoid body as same as shown in the normal cell originated embryoid body, but not always limited thereto.

The comparison in step iv) is performed more preferably to select a sample compound or composition that induces the expression of the vascular cell marker gene or protein in the vascular cells at the similar level to that of the normal cell originated vascular cells but reduces the Gb3 deposit, compared with the non-treated control. It is most preferred to select a sample compound or composition that inhibits the Gb3 deposit in the cells lower than that of the non-treated control, but not always limited thereto.

In another preferred embodiment of the present invention, the inventors investigated whether or not the pharmacologic treatment during the differentiation of FB-iPSC could be effective in improving Fabry disease. To do so, the inventors first induced the differentiation of FB-iPSCs into vascular endothelial cells and vascular smooth muscle cells, to which Fabrazyme, the GLA recombinant protein, was treated. As a result, it was confirmed that the Gb3 deposit was significantly reduced in the FB-iPSCs, vascular endothelial cells, and vascular smooth muscle cells (see FIG. 15).

The Fabry disease originated iPSC model of the present invention demonstrates the same pluripotency as the one that normal iPSCs show, suggesting that it can be efficiently differentiated into embryoid body or vascular cells, but at the same time it does not show the equal level of GLA protein expression and activity which is characteristically observed in Fabry disease patient cells. Accordingly, intracellular Gb3 deposit is observed in this model and the improvement of Fabry disease can be confirmed by observing the decrease of Gb3 deposit by pharmacologic treatment. Therefore, the iPSC model of the present invention can be efficiently used for the screening of therapeutic agent candidates for Fabry disease.

The present invention also provides a use of the Fabry disease iPSC model prepared by the above method.

In addition, the present invention provides a use of iPSCs as a Fabry disease model comprising the following steps:
 i) inducing the differentiation of embryoid body (EB) or vascular cells from the iPSCs prepared above; and
 ii) analyzing the differentiation marker for the embryoid body or the vascular cells induced in step i).

The Fabry disease originated iPSC model of the present invention demonstrates the same gene mutation as shown in Fabry disease patient with showing pluripotency, so that the iPSC model can be effectively used for the study of Fabry disease.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLES

Example 1

Preparation of Induced Pluripotent Stem Cells (iPSCs) Originated from Fabry Disease Patient <1-1> Confirmation of Fabry Disease Causing Gene Mutation To identify the mutation of Fabry disease causing gene in Fabry disease patient, the sequence of α-galactosidase (GLA) gene in the fibroblasts of Fabry disease patient was analyzed.

Particularly, a Fabry disease patient was reported from Asan medical center (Korea). After reviewed by the institutional review board of the center and gotten the agreement from the patient and his legal representative, skin tissue biopsy was performed via punch biopsy method after local anesthesia to obtain dermal tissue from the Fabry disease patient. Then, fibroblasts were separated from the obtained dermal tissue, which were cultured in Dulbecco's modified Eagle's medium (DMEM; GIBCO, USA) supplemented with 10% fetal bovine serum (FBS; GIBCO, USA), 0.05 mg/ml ascorbic acid, 0.3 mg/ml L-glutamine (GIBCO, USA), 3.7 mg/ml sodium bicarbonate ($NaHCO_3$), and 100 U/ml penicillin (GIBCO, USA). Upon completion of the culture, 100 μl of the cell culture supernatant was inoculated in a tissue culture plate, which stood at 37° C. in the presence of 5% $CO_2$ for 3 hours. Then, 2 ml of culture medium was added thereto, followed by culture for 1 week. The viability and proliferation of the fibroblasts cultured above were investigated. Genomic DNA (gDNA) was extracted from the fibroblasts, and GLA gene sequence was analyzed by using the forward primer (SEQ. ID. NO: 1: atgcagctgaggaacccag) and the reverse primer (SEQ. ID. NO: 2: ttaaagtaagtctttaatgacatc). As for the control, H9 cells (ATCC HTB176; American Type Culture Collection (ATCC), USA) were treated by the same manner as described above and then GLA gene sequence therein was confirmed. The result (wild type; WT) was compared with the gene sequence obtained from the Fabry disease patient.

As a result, as shown in FIG. 1, a nonsense mutation on exon 6 was observed in the genomic DNA of Fabry disease patient, suggesting that the $268^{th}$ lysine residue of the GLA protein translated from the gene did not observed because of the mutation (FIG. 1).

<1-2> Development of Fabry Disease Patient Originated iPSCs

To execute the example of the invention, the development of Fabry disease originated iPSCs (FB-iPSCs) was induced from the fibroblasts of Fabry disease patient by ectopic expression (Takahashi, K et al, Cell 131(5): 861-872, 2007) using the reprogramming factors OCT4, SOX2, KLF4, and C-MYC.

Particularly, the fibroblasts obtained from Fabry disease patient were cultured in DMEM supplemented with 10% fetal bovine serum (FBS; GIBCO, USA), 50 U/ml penicillin (GIBCO, USA), 50 mg/ml streptomycin (GIBCO, USA), and 1 mM non-essential amino acid (GIBCO, USA). Then, the development of FB-iPSCs was induced by using the conventional technique well-informed to those in the art, that is the transduction with retrovirus expressing such factors as OCT4, SOX2, KLF4, and C-MYC. The developed FB-iPSCs were confirmed with phase-contrast microscope.

As a result, as shown in FIG. 2, it was confirmed that FB-iPSCs were successfully developed from the fibroblasts of Fabry disease patient, which demonstrated the normal cell like iPSC morphology (FIG. 2).

<1-3> Pluripotency of FB-iPSCs

To confirm the pluripotency of the undifferentiated FB-iPSCs, the expression of the stemness marker in the FB-iPSCs was observed.

Particularly, the FB-iPSCs prepared in Example <1-2> were treated with phosphate buffered saline (PBS) containing 4% formaldehyde, followed by fixing at room temperature for 15 minutes. The cells were treated with 0.1% triton X-100 to give permeability to the cell membrane. After the treatment, the cells were added with 4% normal donkey serum, followed by blocking at room temperature for 1 hour. The cells were treated with the primary antibody such as anti-OCT4 antibody (1:300, R&D Systems, USA), anti-NANOG antibody (1:300, Cell signaling technology, USA), anti-SSEA-4 antibody (1:300, R&D Systems, USA), anti-SOX2 rabbit antibody (BD Transduction Laboratories, USA), anti-Tra-1-81 antibody (1:300, Millipore, USA) or anti-Tra-1-60 antibody (1:300, Millipore, USA), followed by culture overnight at 4° C. Then, the cells were washed several times with PBST (PBS containing 0.1% Tween-20). The cells were treated with Alexa Fluor 488 or Alexa Fluor 594-conjugated secondary antibody (Invitrogen, USA), followed by further culture for 1 hour, leading to immunofluorescent staining of FB-iPSCs.

The cells were observed under fluorescence microscope (Olympus, Japan) or Zeiss LSM 510 confocal microscope (Carl Zeiss, Germany) to investigate the expressions of OCT4, NANOG, SOX2, SSEA4, Tra-1-80, and Tra-1-61 proteins.

As a result, as shown in FIG. 3, almost as normal expressions of the stemness markers OCT4, NANOG, SOX2, SSEA4, Tra-1-80, and Tra-1-61 proteins as in the normal cells were observed in the FB-iPSCs (FIG. 3).

<1-4> Reprogramming in Non-differentiated FB-iPSCs

To investigate whether or not the reprogramming process occurred in the non-differentiated FB-iPSCs after being developed, bisulfite sequencing was performed to confirm DNA demethylation on CpG site in OCT4, REX1, and NANOG gene promoter regions in FB-iPSCs (Park, S. W. et al. (2010) Blood 116, 5762-5772).

Particularly, the genomic DNA was treated with sodium bisulfite by using theEZ DNA methylation-Gold Kit (Zymo Research, USA) according to the manufacturer's protocol. PCR amplification was performed using 25~50 ng of the sodium bisulfite treated DNA as a template. The amplified PCR product was purified by using AccuPrep® plasmid Mini extraction Kit (Bioneer, Korea), followed by subcloning in pGEM-T EASY vector (Promega, USA). Then, the vector was introduced in the fibroblasts and FB-iPSCs and then transfected clones, 5 of each, were obtained. Sequence was analyzed by using M13 primer with the web-based program blast 2 or BiQ analyzer.

As a result, as shown in FIG. 4, it was confirmed that the reprogramming process occurred in the non-differentiated FB-iPSCs after being developed (FIG. 4).

Example 2

Differentiation of Fabry Disease Patient Originated Embryoid Body (EB)

<2-1> Differentiation of Embryoid Body from FB-iPSCs

To investigate the pluripotency of FB-iPSCs in vitro, the differentiation of embryoid body (EB) was induced from FB-iPSCs.

Particularly, the colony of the FB-iPSCs developed by the same manner as described in Example <1-2> was cut into 4 pieces by using McClain tissue chopper. The 4 FB-iPSC sections were distributed in ultra-low attachment dish, which were resuspended in 5 ml of embryoid body differentiation medium, which was DMEM/F12 containing 10% serum replacement (SR), followed by suspension culture for 4 days to induce the differentiation of FB-iPSC originated embryoid body (FB-EB). As for the normal control, WT-iPSCs were cultured by the same manner as described above and therefore WT-iPSC originated embryoid body (WT-EB) was differentiated.

<2-2> Confirmation of Differentiation Potency of FB-EB

To confirm the differentiation potency of FB-EB, the expressions of three germ layer markers, the ectodermal marker N-cadherin, the endodermal marker SOX17, and the mesodermal marker α-smooth muscle actin, were investigated.

Particularly, the FB-EB differentiated by the same manner as described in Example <2-1> was immunofluorescent-stained by the same manner as described in Example <1-3> and then the expressions of N-cadherin, SOX17, and α-smooth muscle actin were investigated. As the primary antibodies for the immunofluorescent staining, anti-N-cadherin mouse antibody (Cell Signaling Technologies, USA), anti-α-smooth muscle actin mouse antibody (R&D, USA), and anti-SOX17 mouse antibody (R&D, USA) were used. To compare the expression level, the cells were treated with 4'6-diamidino-2-phenylindole (DAPI) to stain nuclei.

As a result, as shown in FIG. 5, all of those three germ layer markers, N-cadherin, SOX17, and α-smooth muscle actin, were expressed in FB-EB, suggesting that the FB-EB had pluripotency (FIG. 5).

Example 3

Deficiency of α-galactosidase (GLA) Expression and Decrease of GLA Activity in FB-iPSCs <3-1> Expression of GLA Gene in FB-iPSCs To measure the expression of GLA gene in Fabry disease patient, the level of GLA mRNA in FB-iPSCs was investigated.

Particularly, FB-iPSCs were obtained by the same manner as described in Example <1-2>, which were then suspended in TRIzol (Invitrogen, USA). Total RNA was extracted from the FB-iPSCs according to the manufacturer's protocol. Then, first-strand cDNA of GLA was synthesized from 1 µg of the extracted RNA by using M-MLV reverse transcriptase (Enzynomics, USA) with the forward primer (SEQ. ID. NO: 3: AGCCTGGGCTGTAGCTATGA) and the reverse primer (SEQ. ID. NO: 4: TGCCTGTGGGATTTATGTGA). The synthesized cDNA was amplified, followed by electrophoresis to confirm the expression of GLA gene at RNA level.

As for the normal control, the human fibroblast cell line CRL 2094 (cat No. CCD-1077Sk, ATCC, USA) was infected with OCT4, SOX2, C-MYC, and KLF4, resulting in the preparation of iPSCs (CRL_hiPSCs), which were used as the normal human reprogrammed pluripotent stem cells. H9 cells were used as the normal human embryonic stem cells. The expression of GLA gene in the wild-type cells was also investigated. To correct the expression level, the expression level of α-tubulin gene was measured by the same manner as described above as the control.

As a result, as shown in FIG. 6, the expression level of GLA gene in FB-iPSCs was similar to that in the normal control H9 cells (FIG. 6).

<3-2> GLA Protein Expression in FB-iPSCs

The expression level of GLA protein which was expected to be lack in Fabry disease patient was measured in FB-iPSCs.

Particularly, FB-iPSCs were obtained by the same manner as described in Example <1-2>, which were then suspended in PRO-PREP™ protein extraction solution (iNtRON, Korea). The supernatant containing cellular protein was obtained, followed by brad-fold assay to measure the protein concentration. 20 μg of total protein was separated on 12% SDS-PAGE gel and transferred onto nitrocellulose membrane (Bio-Rad, USA), followed by blocking with TBST (10 mM Tris-HCl (pH 7.5), 150 nM NaCl, and 0.1% Tween-20) composed of Tris-buffered saline (TBS) containing 5% skim milk. Then, the membrane was treated with the primary antibody (anti-rabbit polyclonal GLA antibody, 1:1000, cat #: AP6727a, Abgent, USA), followed by culture at 4° C. for overnight. The membrane was washed with TBST and then treated with the secondary antibody (Goat anti-Rabbit IgG (H+L) Secondary Antibody, horseradish peroxidase (HRP) conjugate; Thermo scientific, USA), followed by culture at room temperature for 1 hour. Then, the membrane was washed and proceeded to Western blotting. The result of the Western blotting was confirmed by the signal detecting the color development using ECL system according to the manufacturer's protocol. As for the normal control, H9 cells were treated by the same manner as described above and the expression level of GLA protein in the wild-type cells was measured. The control to correct the color development was treated with anti-β-actin antibody (1:3000; Santa Cruz, USA) in order to stain β-actin.

As a result, as shown in FIG. 7, the GLA protein expression was confirmed in the normal control, while the GLA protein expression was not detected in FB-iPSCs (FIG. 7).

<3-3> GLA Activity in FB-iPSCs

To investigate the GLA activity according to the lack of GLA protein, the GLA protein activity in FB-iPSCs was measured by the conventional flurogenic method (Benjamin, E. R. et al. *Journal of inherited metabolic disease* 32, 424-440 (2009)).

Particularly, FB-iPSCs were obtained by the same manner as described in Example <1-2>, followed by culture in feeder-free culture MEF-conditioned medium for 5 days. Upon completion of the culture, FB-iPSCs were obtained and washed, to which 200 μl of GLA assay buffer (pH 4.6) containing 100 mM sodium citrate (Sigma, USA) and 200 mM sodium phosphate dibasic (Sigma, USA) was added, followed by sonication programmed to have 1 sec destruction/1 sec rest cycle for total 10 seconds. BCA assay was performed using Micro BCA protein assay kit (Pierce, USA) to quantify the protein in the cell lysate. Then, centrifugation was performed at 4° C. for 30 minutes to obtain the cell lysate supernatant. 30 μl of 200 mM N-acetyl-D-galactosamine (GalNAC; Sigma, USA), 6 μl of 50 mM 4-MU-α-D-galactopyranoside (4MUaGal; Sigma, USA), 14 μl of GLA assay buffer, and 10 μl of the cell lysate supernatant were mixed for the preparation of a mixture for GLA assay. The prepared mixture was loaded in a 96-well plate having black wells with clear-bottom, followed by culture at 37° C. for 1 hour. Upon completion of the culture, 150 μl of GLA stop buffer containing 200 mM glysine (pH 10.32) was added thereto. Fluorescence was measured at 355 and 460 nm by using Victor plate reader (Perkin Elmer, USA). The confirmed fluorescence level was corrected with the standard curve of 4-methylumbelliferon (4-MU) to calculate α-galactosidase activity. As for the normal control, H9 embryonic stem cells were treated by the same manner as described above, and the GLA protein activity in the wild-type cells (H9 ES) was measured.

As a result, as shown in FIG. 8, the GLA activity was confirmed in the normal control. However, the GLA activity was not detected at all in FB-iPSCs, suggesting that GLA was as lack in FB-iPSCs as GLA protein expression was (FIG. 8).

<3-4> Globotriaosylceramide (Gb3, CD77) Deposit in FB-iPSCs

To investigate Gb3 deposit, the most representative characteristics shown in Fabry disease, Gb3 in FB-iPSCs was confirmed by immunofluorescent staining.

Particularly, the FB-iPSCs developed by the same manner as described in Example <1-2> were immunofluorescent-stained by the same manner as described in Example <1-3> to confirm Gb3 therein. As the primary antibody for the immunofluorescent staining, anti-Gb3 antibody (CD77 [38.13], 1:1000; GeneTex, USA) was used. As for the normal control, H9 ES was treated by the same manner as described above and Gb3 deposit in the wild type H9 ES was measured. To compare the expression level, the cells were treated with 4'6-diamidino-2-phenylindole (DAPI) to stain nuclei.

As a result, as shown in FIG. 9, GB3 deposit was not detected in the normal control. However, GB3 deposit was observed in FB-iPSCs, suggesting that FB-iPSCs had the same symptom that was shown in Fabry disease (FIG. 9).

Example 4

Differentiation of FB Originated Vascular Cells

<4-1> Differentiation of Vascular Cells from FB-iPSCs

To induce the differentiation of vascular cells from Fabry disease patient, FB-iPSCs were induced to be differentiated into vascular endothelial cells and vascular smooth muscle cells according to the course illustrated in FIG. 10 (FIG. 10).

Particularly, the FB-iPSCs developed by the same manner as described in Example <1-2> were chopped in even sizes of 300~500 μm in diameter by using a 10 μl syringe needle. Then, the chopped FB-iPSCs were inoculated in Matrigel-coated dish containing mTESR1 medium supplemented with 8 ng/ml of bFGF as the growth factor, followed by culture for 3 days to induce the feeder-free differentiation (step 1). The medium was replaced with RPMI containing 1% B27, to which 50 ng/ml of activin A and 20 ng/ml of BPM4 were added as the growth factors, followed by culture for 3 days to induce the differentiation into mesoderm cells (step 2). Then, the growth factors were replaced with 50 ng/ml of VEGFA and 50 ng/ml of bFGF and the mesodermal cells were cultured in RPMI containing 0.5% B27 for 6 days to induce the differentiation into vascular progenitors (step 3). The differentiated vascular progenitors proceeded to magnetic activated cell sorting (MACS) using CD34 magnetic beads to separate CD34 positive cells that had potential for the differentiation into vascular endothelial cells and vascular smooth muscle cells. The separated CD34 positive vascular progenitors were additionally cultured in EGM-2 medium (Lonza, USA) supplemented with 100 ng/ml of VEGF-A and 100 ng/ml of bFGF as the growth factors for 5~7 days to induce the differentiation into vascular endothelial cells or cultured in EGM-2 medium supplemented with 100 ng/ml of PDGF-BB (R&D, USA) and 100 ng/ml of bFGF as the growth factors for 14~21 days to induce the differentiation into vascular smooth muscle cells (step 4).

As a result, as shown in FIG. 11, the cells expressing CD34 and CD 31 together were developed at least 10% of the vascular progenitors differentiated from FB-iPSCs in step 3) 11 days after the culture (FIG. 11).

<4-2> Morphology of FB-iPSC Originated Vascular Endothelial Cells

To investigate whether or not the Fabry disease originated vascular endothelial cells showed the morphology of normal vascular endothelial cells, the morphology of the FB-iPSC originated endothelial cells was observed.

Particularly, the differentiations of vascular endothelial cells and vascular smooth muscle cells were induced from FB-iPSCs by the same manner as described in Example <4-1>, and then the cell morphology was observed under phase-contrast microscope 16~18 days later.

As a result, as shown in FIG. 12, the differentiated vascular endothelial cells displayed the typical vascular cell like morphology (FIG. 12a), and formed the vascular tube like structure on matrigel (FIG. 12b).

<4-3> Expression of Vascular Endothelial Cell Marker Protein in FB-iPSC Originated Endothelial Cells To confirm if the vascular endothelial cells were successfully differentiated from FB-iPSCs, the expressions of the vascular endothelial cell marker proteins CD31, VE-cadherin (VE-cad), and vWF in the FB-iPSC originated vascular endothelial cells were investigated.

Particularly, the differentiation of vascular endothelial cells was induced by the same manner as described in Example <4-1>. 16~18 days after the differentiation started, immunofluorescent staining was performed by the same manner as described in Example <1-3> to investigate the expressions of CD31, VE-cadherin, and vWF. As the primary antibodies for the immunofluorescent staining, anti-CD31 antibody, anti-VE cadherin antibody (1:100; R&D systems, USA), and anti-vWF antibody (1:100; Abcam, USA) were used. To compare the expression level, the cells were treated with DAPI to stain nuclei.

As a result, as shown in FIG. 13, the vascular endothelial cells differentiated from FB-iPSCs expressed normally the vascular endothelial cell marker proteins CD31, VE-cadherin, and vWF (FIG. 13).

<4-4> Expression of Vascular Endothelial Cell Marker Gene in FB-iPSC Originated Endothelial Cells To confirm if the vascular endothelial cells were successfully differentiated from FB-iPSCs, the expressions of the vascular endothelial cell-specific marker genes ANG2, VE-cad, vWF, EphrinB2, and CAVEOLIN in the FB-iPSC originated vascular endothelial cells were investigated.

Particularly, vascular endothelial cells differentiated by the same manner as described in Example <4-1> were collected. Total RNA was extracted from the vascular endothelial cells by the same manner as described in Example <3-1>, followed by RT-PCR to confirm the expressions of ANG2, VE-cad, vWF, EphrinB2, and CAVEOLIN genes. For the RT-PCR, the primers listed in Table 2 were used. As for the control, H9 embryonic stem cells were induced to be differentiated into vascular endothelial cells by the same manner as described in Example <4-1>, which were used as the normal control (H9-ES). To correct the expression level, the expression of GAPDH gene in the control was measured by the same manner as described above.

As a result, as shown in FIG. 14, the expressions of ANG2, VE-cad, vWF, EphrinB2, and CAVEOLIN genes were not significantly detected in FB-iPSCs. However, the vascular endothelial cell-specific marker gene expression was observed in the endothelial cells differentiated from FB-iPSCs (FB-EC) at the similar level of the normal control (FIG. 14).

Example 5

Improvement of Gb3 Deposit in FB-iPSCs by α-galactosidase

To investigate whether or not the pharmacologic treatment during the FB-iPSC differentiation was effective in improving Fabry disease, the differentiation of vascular cells was induced from FB-iPSCs and then the cells were treated with Fabrazyme, the α-galactosidase recombinant protein.

Particularly, FB-iPSCs were obtained by the same manner as described in Example <1-2>. The differentiations of vascular endothelial cells and vascular smooth muscle cells were induced from FB-iPSCs by the same manner as described in Example <4-1>. The obtained FB-iPSCs, vascular endothelial cells, and vascular smooth muscle cells were treated respectively with 10 μg/ml of Fabrazyme for 5 days. Immunofluorescent staining was performed by the same manner as described in Example <1-3> to confirm Gb3 therein. The primary antibody for the immunofluorescent staining was anti-Gb3 antibody. For the control to confirm the differentiation of vascular endothelial cells or vascular smooth muscle cells from FB-iPSCs, anti-CD31 antibody or anti-α-SMA antibody (1:100; R&D systems, USA) was used. To compare the expression level, the cells were treated with DAPI to stain nuclei.

As a result, as shown in FIG. 15, Gb3 deposit was confirmed in FB-iPSCs, vascular endothelial cells, and vascular smooth muscle cells before the treatment of Fabrazyme. However, after the treatment of Fabrazyme (10 μg/ml) for 5 days, Gb3 deposit was significantly reduced and hardly detected (FIG. 15).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for preparing a Fabry disease model in vitro comprising vascular cells, wherein the method comprises:
   i) obtaining dermal tissue from a Fabry disease human patient and separating fibroblasts from the dermal tissue of the patient;
   ii) inducing formation of induced pluripotent stem cells (iPSCs) from the fibroblasts separated from the Fabry disease patient in vitro by ectopic expression of a pluripotent marker;
   iii) collecting the iPSCs induced in step ii); and
   iv) inducing differentiation of vascular cells from the iPSCs, thereby producing a Fabry disease model comprising vascular cells.

2. The method of claim 1, wherein the pluripotent marker is OCT4, SOX2, KLF4 or C-MYC.

3. The method of claim 1, wherein the iPSCs:
   i) express one or more pluripotency markers selected from the group consisting of OCT4, NANOG, SOX2, SSEA4, Tra-1-80, and Tra-1-61;
   ii) express α-galactosidase (GLA) gene;
   iii) are unable to express GLA protein;
   iv) lack GLA enzyme activity; or
   v) show intracellular globotriaosylceramide (Gb3, CD77) deposit.

4. The method of claim 1, further comprising:
   analyzing a differentiation marker of the vascular cells induced in step iv).

5. The method of claim 4, wherein the differentiation marker is selected from the group consisting of an ectodermal marker N-cadherin, an endodermal marker SOX17, and an mesodermal marker a-smooth muscle actin.

6. The method of claim 4, wherein the vascular cells are vascular endothelial cells or vascular smooth muscle cells.

7. The method of claim 6, wherein the vascular endothelial cells are characterized by one or more characteristics, and wherein the characteristics are:
   a) having vascular tube-like structure;
   b) expressing one or more of CD31, VE-cadherin, and vWF; and
   c) expressing one or more of ANG2, VE-cad, vWF, EphrinB2, and CAVEOLIN.

8. The method of claim 7, further comprising screening one or more therapeutic agent candidates for Fabry disease by:
   i) treating the vascular cells with a test therapeutic agent compound or composition;
   ii) analyzing the effect of the test therapeutic agent compound or composition on one or more characteristics of the vascular cells, wherein the characteristics are:

a) forming a vascular tube-like structure;
b) showing reduced Gb3 deposit;
c) expressing one or more of CD31, VE-cadherin, and vWF; and
d) expressing one or more of ANG2, VE-cad, vWF, EphrinB2, and CAVEOLIN; and iii) comparing the characteristics of the treated vascular cells with the same characteristics in non-treated control vascular cells, thereby identifying the test therapeutic agent compound or composition as a therapeutic agent candidate for Fabry disease.

9. The method of claim 8, wherein the vascular cells are vascular endothelial cells or vascular smooth muscle cells.

10. The method of claim 5, wherein the differentiation marker is SOX17.

11. The method of claim 6, wherein the vascular cells are vascular endothelial cells.

12. The method of claim 11, wherein the vascular endothelial cells express CD31.

* * * * *

SEQUENCE LISTING

<160> NUMBER OF SEQ ID NOS: 4

<210> SEQ ID NO 1

```
<211> LENGTH: 19
<212> TYPE: DNA
<213> ORGANISM: Artificial Sequence
<220> FEATURE:
<223> OTHER INFORMATION: primer

<400> SEQUENCE: 1
atgcagctga ggaacccag                                                  19

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
ttaaagtaag tcttttaatg acatc                                           25

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
agcctgggct gtagctatga                                                 20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tgcctgtggg atttatgtga                                                 20
```